(12) United States Patent
Gkoulalas-Divanis et al.

(10) Patent No.: US 10,770,171 B2
(45) Date of Patent: Sep. 8, 2020

(54) AUGMENTING DATASETS USING DE-IDENTIFIED DATA AND SELECTED AUTHORIZED RECORDS

(71) Applicant: International Business Machines Corporation, Armonk, NY (US)

(72) Inventors: Aris Gkoulalas-Divanis, Waltham, MA (US); Corville O. Allen, Morrisville, NC (US)

(73) Assignee: International Business Machines Corporation, Armonk, NY (US)

(*) Notice: Subject to any disclaimer, the term of this patent is extended or adjusted under 35 U.S.C. 154(b) by 134 days.

(21) Appl. No.: 15/951,260

(22) Filed: Apr. 12, 2018

(65) Prior Publication Data
US 2019/0318809 A1   Oct. 17, 2019

(51) Int. Cl.
*G06F 21/62* (2013.01)
*G16H 10/20* (2018.01)

(52) U.S. Cl.
CPC .......... *G16H 10/20* (2018.01); *G06F 21/6254* (2013.01)

(58) Field of Classification Search
CPC .................... G16H 10/20; G06F 21/6254
See application file for complete search history.

(56) References Cited

U.S. PATENT DOCUMENTS

| 7,251,609 B1 | 7/2007 | McAlindon et al. |
| 7,493,319 B1 | 2/2009 | Dash et al. |
| 7,512,541 B2 | 3/2009 | Stroup et al. |
| 7,519,591 B2 | 4/2009 | Landi et al. |
| 7,711,580 B1 | 5/2010 | Hudson |
| 8,140,502 B2 | 3/2012 | Francis et al. |
| 8,347,101 B2 | 1/2013 | Wilson |

(Continued)

FOREIGN PATENT DOCUMENTS

WO   2017205544 A1   11/2017

OTHER PUBLICATIONS

List of IBM Patents or Patent Applications Treated as Related, filed Jun. 24, 2019.

(Continued)

*Primary Examiner* — Joseph P Hirl
*Assistant Examiner* — Stephen T Gundry
(74) *Attorney, Agent, or Firm* — Will Stock; Edell, Shapiro & Finnan, LLC

(57) ABSTRACT

A computer system utilizes a dataset to support a research study. One or more regions of interestingness are determined within a model of a first set of data records that are authorized for the research study by associated entities. A second set of data records is represented within the model, wherein the second set of data records are relevant for supporting objectives of the research study after de-identification. Records from the second dataset that are particularly useful for supporting objectives of the research study are identified, and authorization is requested from the corresponding entities of the identified data records from the second set of data records. After receiving authorization, those records are included with the first set to generate a resulting dataset. Embodiments of the present invention further include a method and program product for processing requests for health information in substantially the same manner described above.

14 Claims, 5 Drawing Sheets

(56) References Cited

U.S. PATENT DOCUMENTS

| | | | |
|---|---|---|---|
| 8,494,874 B2 | 7/2013 | Green, III et al. | |
| 8,880,532 B2 | 11/2014 | Shyr et al. | |
| 8,984,098 B1 | 3/2015 | Tomkins et al. | |
| 8,996,474 B2 | 3/2015 | Binkowski et al. | |
| 9,087,215 B2 | 7/2015 | LaFever et al. | |
| 9,118,641 B1 | 8/2015 | Paris, III | |
| 9,202,066 B2 | 12/2015 | Sinderbrand et al. | |
| 9,336,532 B1 | 5/2016 | Barton et al. | |
| 9,361,481 B2 | 6/2016 | LaFever et al. | |
| 9,619,669 B2 | 4/2017 | LaFever et al. | |
| 9,760,298 B2 | 9/2017 | Andrews et al. | |
| 9,760,718 B2 | 9/2017 | Braghin et al. | |
| 9,773,124 B2 | 9/2017 | El Emam et al. | |
| 9,779,077 B2 | 10/2017 | van den Broek | |
| 9,779,146 B2 | 10/2017 | Thatavarthy et al. | |
| 9,842,138 B2 | 12/2017 | Rabolt et al. | |
| 9,846,836 B2 | 12/2017 | Gao et al. | |
| 9,965,651 B1 | 5/2018 | Paris, III | |
| 10,043,035 B2 | 8/2018 | LaFever et al. | |
| 10,454,901 B2* | 10/2019 | Kho | G06F 21/6254 |
| 10,566,082 B1* | 2/2020 | McNair | G06F 16/955 |
| 10,572,684 B2* | 2/2020 | LaFever | G16H 10/60 |
| 10,622,101 B1 | 4/2020 | Dunlap et al. | |
| 2001/0051882 A1 | 12/2001 | Murphy et al. | |
| 2002/0000247 A1 | 1/2002 | Cusac et al. | |
| 2005/0256380 A1* | 11/2005 | Nourie | G06Q 10/10 600/300 |
| 2005/0273367 A1 | 12/2005 | Nourie et al. | |
| 2006/0059189 A1 | 3/2006 | Dunki et al. | |
| 2007/0118399 A1 | 5/2007 | Avinash et al. | |
| 2007/0245144 A1* | 10/2007 | Wilson | G06F 21/6254 713/170 |
| 2010/0250285 A1* | 9/2010 | Shelton | G06F 21/6254 705/3 |
| 2011/0112970 A1* | 5/2011 | Yu | G06F 21/6254 705/51 |
| 2011/0258000 A1* | 10/2011 | Green, III | G06Q 10/06 705/3 |
| 2011/0264466 A1* | 10/2011 | Green, III | G06Q 10/06 705/3 |
| 2013/0304542 A1* | 11/2013 | Powell | G16H 10/60 705/7.32 |
| 2014/0289001 A1 | 9/2014 | Shelton | |
| 2015/0039611 A1 | 2/2015 | Deshpande et al. | |
| 2015/0128284 A1 | 5/2015 | LaFever et al. | |
| 2015/0128285 A1* | 5/2015 | LaFever | G06F 21/6254 726/26 |
| 2015/0128287 A1 | 5/2015 | LaFever et al. | |
| 2015/0161336 A1 | 6/2015 | Kalathil | |
| 2015/0339496 A1 | 11/2015 | El Emam et al. | |
| 2015/0379303 A1 | 12/2015 | LaFever et al. | |
| 2016/0085880 A1 | 3/2016 | Sheffer et al. | |
| 2016/0110523 A1* | 4/2016 | Francois | G06Q 50/24 705/2 |
| 2016/0283745 A1 | 9/2016 | LaFever et al. | |
| 2017/0004594 A1 | 1/2017 | Gliklich et al. | |
| 2017/0046447 A1 | 2/2017 | Peng et al. | |
| 2017/0091388 A1 | 3/2017 | Zolla et al. | |
| 2017/0091412 A1* | 3/2017 | Johnson | H04W 4/80 |
| 2017/0091686 A1 | 3/2017 | Goyal | |
| 2017/0169252 A1 | 6/2017 | Ukena-Bonfig et al. | |
| 2017/0208041 A1 | 7/2017 | Kho et al. | |
| 2017/0243028 A1 | 8/2017 | LaFever et al. | |
| 2017/0255790 A1 | 9/2017 | Barrett et al. | |
| 2017/0286556 A1 | 10/2017 | Chan et al. | |
| 2017/0301041 A1 | 10/2017 | Schneider | |
| 2017/0351845 A1* | 12/2017 | Poppa | G06F 19/3418 |
| 2018/0018590 A1* | 1/2018 | Szeto | G06N 20/00 |
| 2018/0082022 A1* | 3/2018 | Francois | G06Q 10/10 |
| 2018/0092595 A1 | 4/2018 | Chen et al. | |
| 2018/0182470 A1* | 6/2018 | Kalathil | G16H 10/60 |
| 2018/0307859 A1 | 10/2018 | LaFever et al. | |
| 2019/0096511 A1* | 3/2019 | Longmire | G16H 10/20 |
| 2019/0156927 A1* | 5/2019 | Virkar | G16H 15/00 |
| 2019/0205507 A1 | 7/2019 | Antonatos et al. | |
| 2019/0304575 A1* | 10/2019 | Beltre | G16H 50/30 |
| 2019/0318124 A1 | 10/2019 | Gkoulalas-Divanis | |
| 2019/0318125 A1 | 10/2019 | Gkoulalas-Divanis | |
| 2019/0318810 A1 | 10/2019 | Gkoulalas-Divanis et al. | |
| 2019/0318811 A1 | 10/2019 | Gkoulalas-Divanis | |
| 2019/0318813 A1 | 10/2019 | Gkoulalas-Divanis | |
| 2019/0332807 A1 | 10/2019 | LaFever et al. | |

OTHER PUBLICATIONS

Webberley et al.; "Retweeting Beyond Expectation: Inferring Interestingness in Twitter", Computer Communications, vol. 73, Part B, Jan. 1, 2016, pp. 229-235.

Tsai et al.; "Person-Specific Domian Adaptation With Applications to Heterogeneous Face Recognition", ICIP IEEE International Conference on, Oct. 27-30, 2014, pp. 338-342.

Nelson, S. Gregory; "Practical Implications of Sharing Data: A Primer on Data Privacy, Anonymization, and De-Identification", ThotWare Technologies, Mar. 28, 2015, pp. 1-23.

Garfinkel, L. Simson; "De-Identification of Personal Information", U.S. Department of Commerce, National Institute of Standards and Technology, Oct. 30, 2015, pp. 1-54.

Bernard et al.; "Visual-Interactive Exploration of Interesting Multivariate Relations in Mixed Research Data Sets", EuroVis Conference on, vol. 33, Issue 3, Jun. 2014, pp. 291-300.

Rabkin et al.; "A Graphical Representation for Identifier Structure in Logs", SLAML'10 ACM Workshop on, Oct. 10, pp. 1-9.

Christopher et al.; "Knowledge-Based Systems and Interestingness Measures: Analysis With Clinical Datasets", CIT Journal of, vol. 24, No. 1, Mar. 2016, pp. 65-78.

Sahar, Sigal; "What Is Interesting: Studies on Interestingness in Knowledge Discovery", Tel-Avis University, Doctoral Dissertation, Mar. 2003, pp. 1-200.

"Use of Patient Information for Single Case Studies and Journal Publication", hipaa@u.washington.edu, UW Medicine Compliance, 2014, 1 page.

Black, "Temporal Data Mining in Electronic Medical Records from Patients with Acute Coronary Syndrome", University of Washington, 2013, 113 pages.

Anonymously, "A Method and System for Storing and Viewing Patient Medical Images in a Personal Health Record Store", http://ip.com/IPCOM/000251246D, Oct. 26, 2017, 5 pages.

Anonymously, "Universal Blockchained Health Record", http://ip.com/IPCOM/000245863D, Apr. 13, 2016, 3 pages.

Anonymously, "A Method and System for Automatically Selecting Patient Cohorts from Electronic Health Records using Flexible Search and an Automatic Longitudinal Patient Record Formation", http://ip.com/IPCOM/000241430D, Apr. 25, 2015, 6 pages.

"Data De-identification and Anonymization of Individual Patient Data in Clinical Studies—A Model Approach", Transcelerate BioPharma Inc., 2013, 15 pages.

List of IBM Patents or Patent Applications Treated as Related, Nov. 2018, 1 page.

\* cited by examiner

AUGMENTING DATASETS USING DE-IDENTIFIED DATA AND SELECTED AUTHORIZED RECORDS

BACKGROUND

1. Technical Field

Present invention embodiments relate to data mining, and more specifically, to identifying and augmenting datasets for research with de-identified data and with data from recommended records upon receiving authorization from subject entities.

2. Discussion of the Related Art

Research studies may require the collection and analysis of large volumes of personal data from many entities. To obtain personal data, researchers may ask entities for their consent to share their data for a stated purpose, such as a particular medical study. Entities who agree to provide their personal data may consent to sharing only a subset of their personal data, or stipulate that their personal data be used for limited or enumerated purposes only.

Often, it is difficult to find enough participants who are willing to contribute their personal information for a study. In order to create larger and richer datasets, researchers may desire to include data from elsewhere in a manner that supports the study.

SUMMARY

According to one embodiment of the present invention, a computer system utilizes a dataset to support a research study. One or more regions of interestingness are determined within a model of a first set of data records that are authorized for the research study by associated entities. A second set of data records is represented within the model, wherein the second set of data records are relevant for supporting objectives of the research study, correspond to entities other than those associated with the first set of data records, and are used after de-identification according to de-identification requirements or authorization by corresponding entities. Records from the second dataset that have greater relevance for supporting objectives of the research study are identified, and authorization is requested from the corresponding entities of the identified data records from the second set of data records. After receiving authorization, those records are included with the first set to generate a resulting dataset. Embodiments of the present invention further include a method and program product for processing requests for health information in substantially the same manner described above.

BRIEF DESCRIPTION OF THE DRAWINGS

Generally, like reference numerals in the various figures are utilized to designate like components.

DETAILED DESCRIPTION

Present invention embodiments relate generally to controlling data access by creating datasets for research that contain data provided by entities with their consent, and more specifically, to augmenting such datasets with de-identified data and with data from recommended records upon receiving the authorization of the subject entities. In general, research studies benefit from larger samples sizes of data. However, it may be difficult for researchers to find enough entities (e.g., individuals, groups of individuals, business entities, etc.) whose records are relevant for a particular study and who are also willing to participate. At the same time, many other entities have made their personal data available to be used for any purpose, as long as the data is sufficiently de-identified first so that the entities can remain anonymous. Larger and richer datasets may be generated for particular research purposes by augmenting the smaller datasets composed of consenting participants' data with data provided for any research purpose in general. However, for general-purpose data to be included, it must be relevant to the research purpose. Present invention embodiments augment smaller datasets by finding general-purpose data that is relevant, and furthermore, by recommending particular data records in the general-purpose data that are suitable for the research study if consent from the corresponding entities is granted.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 1:
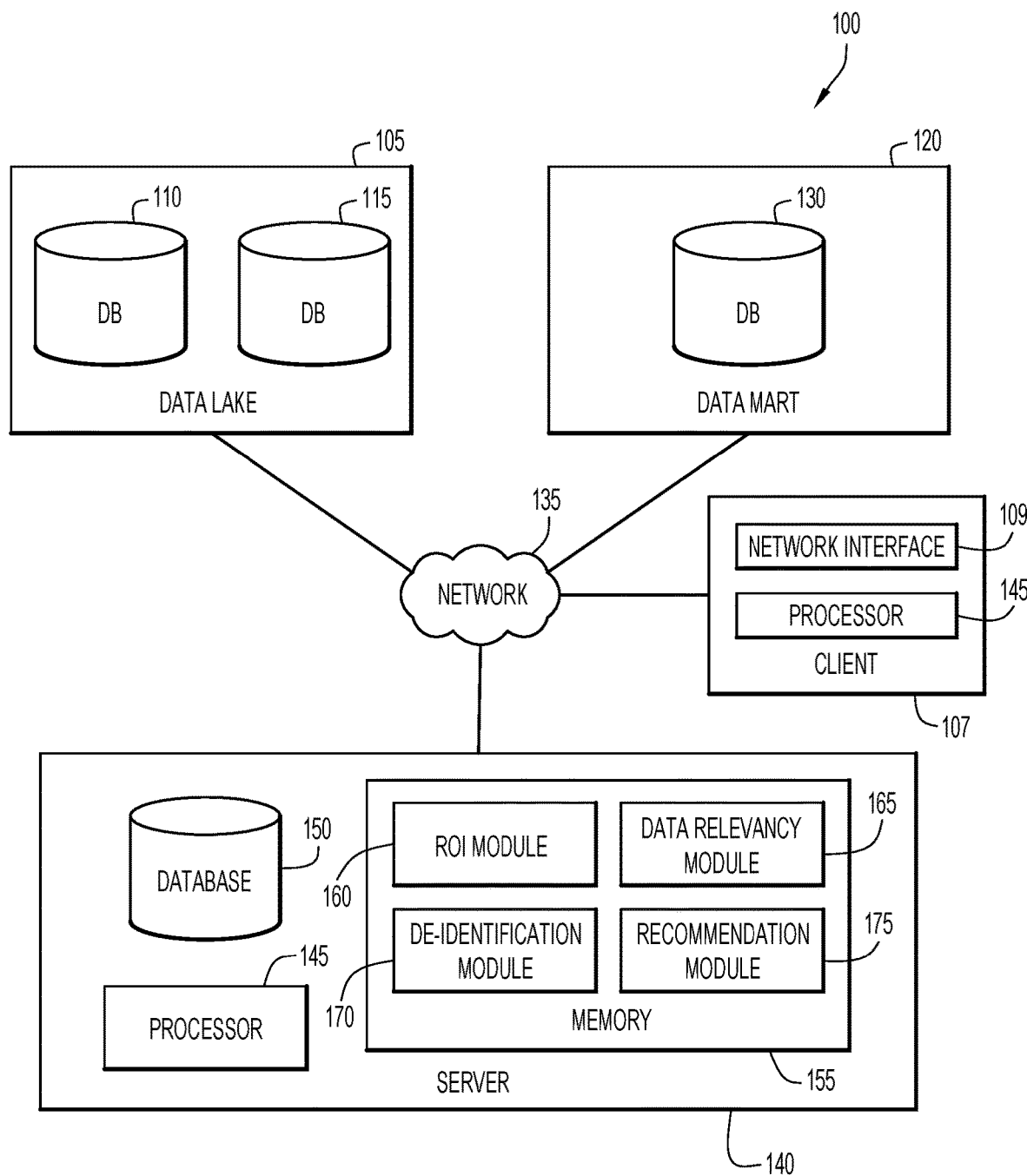
FIG. 1 is a block diagram depicting a computing environment for generating datasets in accordance with an embodiment of the present invention.

Present invention embodiments will now be described in detail with reference to the Figures. FIG. 1 is a block diagram depicting a computing environment 100 for generating datasets in accordance with an embodiment of the present invention. As depicted, computing environment 100 includes a data lake 105 with databases 110 and 115, a data mart 120 with a database 130, a network 135, a client 107, and a server 140. The server includes a processor 145, a database 150, and a memory 155 with a region-of-interestingness module 160, a data relevancy module 165, a de-identification module 170, and a recommendation module 175 Computing environment 100 may enable the augmentation of datasets provided from participants who consented to the data's use for limited research purposes with datasets provided by entities for any purpose.

Data lake 105 may store personal data in one or more databases, such as database 110 and database 115. Data lake 105 may include storage repositories that contain amounts of raw data in its native format. In some embodiments, data lake 105 stores data according to a flat (rather than hierarchical) storage architecture. Database 110 may store personal data that entities have submitted for one or more specific purposes, such as for the inclusion in certain medical studies. Consent information, which states the specific purpose(s) for which the data may be used, may also be stored along with the specific-purpose data. Database 115 may store personal data that entities have provided for general use toward any research purpose, as long as the data is de-identified prior to use. Since data lake 105 may store original data that has not been de-identified or anonymized, data lake 105 may be subject to various data security regulations. For example, data lake 105 may be a secure storage environment in compliance with the Health Insurance Portability and Accountability Act (HIPAA).

Data mart 120 may store data that is organized in support of a particular research purpose. In some embodiments, data mart 120 enables users to access one or more datasets that have been augmented with de-identified data. Data mart 120 may store each dataset on database 130. A dataset stored on database 130 may include the records of entities who have consented to their personal data being used for a particular purpose (i.e., the purpose toward which data mart 120 is organized), along with de-identified data that supplements the personal data.

Network 135 may include a local area network (LAN), a wide area network (WAN) such as the Internet, or a combination of the two, and includes wired, wireless, or fiber optic connections. In general, network 135 can be any combination of connections and protocols that will support communications between data lake 105, data mart 120, client 107, and/or server 140 in accordance with embodiments of the present invention.

Client 107 includes a network interface 109 and a processor 145. In various embodiments of the present invention, client 107 may include a laptop computer, a tablet computer, a netbook computer, a personal computer (PC), a desktop computer, a personal digital assistant (PDA), a smart phone, a thin client, or any programmable electronic device capable of executing computer readable program instructions. Client 107 may include internal and external hardware components, as depicted and described in further detail with respect to FIG. 4. A user, such as a data owner, may use client 107 to access and manage databases, such as database 110, 115, and 130, as well as create augmented datasets in accordance with embodiments of the present invention.

In general, server 140 and its modules may analyze data provided by entities for a specific purpose, identify additional general-purpose data that can augment the specific-purpose data, and produce new datasets by merging the specific-purpose data with a subset of the general-purpose data. Server 140 may retrieve specific-purpose data from database 110 and general-purpose data from database 115 via network 135. In some embodiments, server 140 stores the retrieved specific-purpose data and/or general-purpose data locally in database 150. At least one processor, such as processor 140, executes the instructions of the modules stored in memory 155. De-identification server 140 may include internal and external hardware components, as depicted and described in further detail with respect to FIG. 5.

Region-of-interestingness (ROI) module 160 may identify particular regions of interestingness in the specific-purpose data. ROI module 160 may find regions of interestingness by searching for records that are statistically correlated as determined according to conventional or other techniques. For example, ROI module 160 may identify regions of interestingness by identifying data records that are clustered together, or that can be partitioned into the same region together according to one or more rule sets. A region of interestingness may be the result of applying a particular query to a dataset.

In some embodiments, the utility requirements of a study create parameter constraints that restrict where ROI module 160 may locate regions of interestingness. For example, if a study is researching the effects of diabetes on individuals over thirty years of age, then ROI module 160 may omit from consideration any records or regions whose age value is below thirty. This ensures that ROI module 160 does not identify a cluster of records as a region of interestingness, since including the records would violate the utility requirements of the study.

Data relevancy module 165 may analyze general-purpose data to identify a subset of records that can be used to support the purpose of the specific-purpose data, and falls within one or more regions of interestingness identified by ROI module 160. Furthermore, data relevancy module 165 may perform de-duplication by excluding any records in the general-purpose data that are also represented in the specific-purpose data.

De-identification module 170 may apply one or more de-identification techniques to the general-purpose data in order to remove direct identifiers and quasi-identifiers. Direct identifiers, also known as personal identifiers, may immediately identify entities without requiring any other information. For example, direct identifiers may include a full name, social security number, telephone number, email or residential address, or other national identifiers. Quasi-identifiers are pieces of information that alone are not sufficient to re-identify an individual, but in combination with other features of the data may provide sufficient information to enable an attacker to uniquely identify an entity. Thus, quasi-identifiers can indirectly identify an individual. For example, the combination of the five-digit zip code where a person lives, together with gender information and the date of birth of the individual, have been shown to be sufficient information to re-identify a large portion of the population of the United States. By performing various de-identification techniques, de-identification module 170 can ensure that a resulting dataset will be in compliance with particular privacy regulations or standards. In some embodiments, de-identification module 170 parallelizes the de-identification of records. For example, the regions of interestingness may be de-identified in parallel. When records are de-identified at the same time, the overall time that the records occupy system memory is reduced, as well as the amount of time required by the de-identification process.

Data may be de-identified as per the requirements of a selected legal privacy framework (e.g., Health Insurance Portability and Accountability Act (HIPAA) Safe Harbor, HIPAA Expert Determination, General Data Protection Regulation (GDPR) pseudonymization, GDPR anonymization, etc.), or by general data de-identification approaches. Forms of de-identification may include data generalization, data suppression, data masking, support of a privacy model such as k-diversity, l-diversity, $\rho_1$-to-$\rho_2$ privacy, $\varepsilon$-differential privacy, $k^m$-anonymity, set-based anonymization, RT-anonymity, or any other data de-identification methodology or combination thereof. In some embodiments, de-identification requirements may include increasing the level of granularity for an entry in a field. For example, each field of a record may have a defined ontology tree of levels of granularity, and de-identification may involve moving up one or more of those levels. Records may be de-identified by generalizing a number between a range (e.g., 32 years of age becomes 30-35 years of age); the range may span a particular subset of values such that it does not violate the region of interestingness containing the record. De-identification module 170 may output de-identified data to any storage, such as storage 150 of server 140 or to storage 130 of data mart 120.

Recommendation module 175 may analyze a subset of the general-purpose data to determine if any of the records are relevant to the subject research study. Recommendation module 175 may analyze general-purpose data records that fall inside of a region of interestingness but cannot be de-identified (e.g., by de-identification module 170). Some data records cannot be de-identified because there is a lack of sufficient other records in the region of interestingness to which it belongs. For example, if a record is de-identified according to a k-anonymity privacy model, and there are not k-1 other records in the same region of interestingness, then the record cannot be de-identified. If a data record cannot be de-identified, the record may be considered a candidate for inclusion in a study, as it can still provide data that is useful to a study upon obtaining the consent of the corresponding entity. Once such candidate records are recommended by recommendation module 175, researchers may contact the corresponding entities and ask them to provide consent for their personal information to be used in a study.

Recommendation module 175 may also analyze general-purpose data records that fall outside of a region of interestingness. For example, if a record is isolated, between two or more regions of interestingness, or near other records that are outside of a region of interestingness yet form their own cluster, the record may be a candidate for inclusion in a study. In some embodiments, recommendation module 175 recommends records that are outside of a region of interestingness as candidates according to one or more rule sets. Once such candidate records are recommended by recommendation module 175, researchers may contact the corresponding entities and ask them to provide consent for their records to be used in a study.

Databases 110, 115, 130, and 150 may include any non-volatile storage media known in the art. For example, databases 110, 115, 130, and 150 can be implemented with a tape library, optical library, one or more independent hard disk drives, or multiple hard disk drives in a redundant array of independent disks (RAID). Similarly, data on databases 110, 115, 130, and 150 may conform to any suitable storage architecture known in the art, such as a file, a relational database, an object-oriented database, and/or one or more tables.

Figure 2:
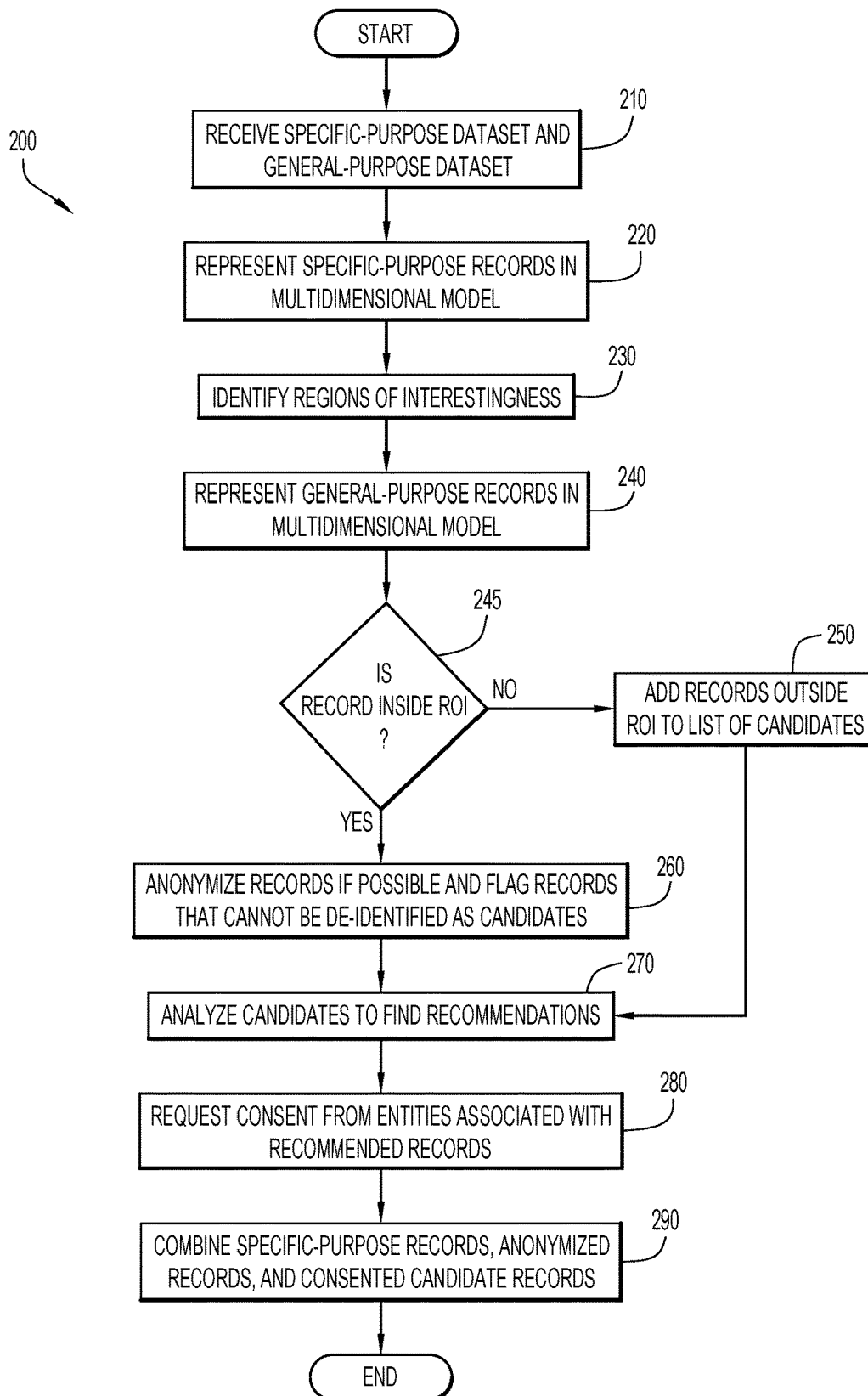
FIG. 2 is a flow chart depicting a method of generating a dataset in accordance with an embodiment of the present invention.

FIG. 2 is a flow chart depicting a method of generating a dataset in accordance with an embodiment of the present invention.

A specific-purpose dataset and general-purpose dataset are received at operation 210. The specific-purpose dataset may contain records that the corresponding entities have granted permission to be used for a particular study. The general-purpose dataset contains records that entities have granted permission for use in any study, as long as the records are first de-identified to preserve the anonymity of the corresponding entities. The specific-purpose dataset may be stored in database 110 or database 150 and may be received by ROI module 160. The general-purpose dataset may be stored in database 115 or database 150 and may be received by ROI module 160. Metadata that describes the level of granularity at which an entity has agreed to share their data may accompany the specific-purpose data.

Specific-purpose data may be obtained from entities who have consented to its use for one or more particular purposes. For example, individuals may consent to the use of any of their health data for the purpose of conducting cardiovascular-related research. Individuals may also control the level of granularity at which they consent to their personal data's use. For example, individuals may provide only their blood pressure data, only their heart rate data, etc., toward cardiovascular-related research.

Granularity levels may be hierarchical; for example, individuals may consent to providing their birth date, or their month and year of birth, or only their birth year. In one embodiment, individuals exert control over the level of granularity according to the number of digits of a medical diagnosis code that are provided. When all of the digits of a diagnosis code are provided, the highest level of specificity for a medical condition is known; if some digits of a code are omitted, a condition may be described more broadly and with less detail. For example, a full diagnosis code may describe a specific type of nearsightedness, a partial diagnosis code may describe nearsightedness in general (e.g. a family of related conditions), and an even more incomplete diagnosis code may simply indicate a reference to a vision disorder. Individuals may also choose whether or not to consent to including any direct identifiers or quasi-identifiers included in their personal data.

The specific-purpose dataset is represented in a multidimensional model at operation 220. Each dimension of a multidimensional model may correspond to a particular direct identifier or quasi-identifier. For an example using the quasi-identifiers of age and gender, a two-dimensional model may be constructed with one axis corresponding to age and the other axis corresponding to gender. Age and gender information in the specific-purpose dataset may then be represented in the multidimensional model. In some embodiments, ROI module 160 constructs a multidimensional model for a specific-purpose dataset and migrates the data to the model. A multidimensional model may have three or more dimensions. In some embodiments, each dimension of a multidimensional model corresponds to one quasi-identifier field of the specific-purpose dataset. Thus, a multidimensional model uses quasi-identifiers as constraints by which individual records are organized in order to identify regions of interestingness. A multidimensional model may be an abstraction of the specific-purpose dataset that uses quasi-identifiers as constraints by which individual records are organized and regions of interestingness are subsequently identified.

Regions of interestingness are identified at operation 230. Each region of interestingness may correspond to a grouping of records in the multidimensional model that are correlated in some manner. ROI module 160 may identify regions of interestingness in the multidimensional model by directly analyzing the underlying dataset using quasi-identifiers as constraints to find records that are statistically related to each other.

In some embodiments, regions of interestingness may be identified by using information related to the purpose or goal of a research study. For example, if the purpose of a genome-wide study is to look into a relation between diagnosis codes and single nucleotide polymorphisms, then the attributes of diagnoses codes and gene sequences should be considered when identifying regions of interestingness. However, if the purpose of a research study does not indicate potential patterns in the data that could lead to the identification of regions of interestingness, then regions of interestingness may nevertheless be identified according to similarities that exist among the various attributes of the data records. For example, regions of interestingness may be identified by searching for data records that are clustered together or by performing frequent item-set mining. Specific data mining or statistical analysis algorithms may identify regions of interestingness that are relevant to the task that the overall dataset is being used to support (e.g., identify regions of interestingness using clustering data if the dataset is planned to be used for clustering purposes, discover outliers if part of the dataset's planned use involves outliers, etc.). ROI module 160 may apply conventional or other data mining techniques to discover regions of interestingness.

In one embodiment, regions of interestingness are identified by representing the specific-purpose data records as a multidimensional model with each dimension corresponding to a quasi-identifier. Next, the data is processed by one or more data analysis algorithms that are relevant to a purpose that needs to be supported by the data. In some embodiments, the data analysis algorithm is similar to (or identical to) an algorithm that will eventually be applied to a dataset resulting from the union of the specific-purpose data and the subset of the general-purpose data. While the algorithm processes the data, a monitoring service (such as data relevancy module 165) monitors the algorithm to determine how the algorithm processes the dataset to support the intended type of analysis; regions of interestingness can be extracted based on observation of the algorithm. For example, if it is known that a certain algorithm will be applied to the resulting dataset (e.g., a dataset that includes the specific-purpose data and the subset of the general-purpose data that is relevant), then that algorithm may be applied to the specific-purpose data only, and by analyzing the records with which the algorithm interacts, regions of interestingness may be identified. Furthermore, utility constraints may be derived, which correspond to regions of interestingness that must be preserved in order to support the purpose of the dataset. The utility restraints may serve as guidelines to ensure that data will support its intended purpose when it is de-identified.

The general-purpose dataset is represented in the multidimensional model at operation 240. Prior to representing the general-purpose data records in the multidimensional model, some records of the general-purpose data may be excluded. Data relevancy module 165 may remove unnecessary duplicate records by excluding any records in the general-purpose data that are also represented in the specific-purpose data. Any records in the general-purpose data that do not support the purpose of the specific-purpose dataset may also be excluded. For example, if the specific-purpose dataset consists of data that is provided for the purpose of studying a certain disease in a particular country, then any records in the general-purpose dataset that do not include that disease and/or country may be excluded. By excluding records prior to matching the general-purpose data to the regions of interestingness, less processing time is required to determine the relevancy of general-purpose data records.

Each of the remaining general-purpose records is analyzed to determine whether it falls inside or outside of a region of interestingness at operation 245. Records in the general-purpose data may be matched to regions of interestingness by determining whether a record of the general-purpose dataset would fall into a region of interestingness if the record were included in the specific-purpose dataset.

Each general-purpose record that does not fall within a region of interestingness is added to a list of candidate records at operation 250. Candidate records from the general-purpose dataset are records that may ultimately be included in the augmented dataset despite not falling within one of the regions of interestingness. Each candidate record may be analyzed by recommendation module 175 at operation 270 in order to determine if it will be included in the augmented dataset.

The general-purpose records that fall within a region of interestingness are de-identified at operation 260. In some embodiments, de-identification module 170 de-identifies the subset of general-purpose data by removing direct identifiers and quasi-identifiers. De-identification may be performed on records that lie within a particular region of interestingness; records should not be de-identified across regions because doing so may obscure underlying patterns in the specific-purpose data that may be of interest to researchers. De-identification may be achieved by generalizing records to have the property of k-anonymity. Records that cannot be de-identified (e.g., when attempting to generalize the records, but there are not k−1 other records in a region) may be denoted as candidate records, which will be considered for inclusion in the augmented dataset.

The candidate records are analyzed to find recommendations at operation 270. The candidate records may include the candidate records that are outside of the regions of interestingness (i.e., the candidates determined at operation 250) as well as the candidate records that are inside of a region of interestingness (i.e., the candidates determined at operation 260). Recommendation module 175 may analyze the candidate records to determine which records are suited for particular data analytic tasks and are therefore recommended for inclusion in the augmented dataset.

Recommendation module 175 may recommend a candidate record if the record is outside of any region of interestingness, but is near one or more regions of interestingness. Such records may be useful because they suggest that there can be other regions of interestingness in between (or overlapping) the nearby region(s) of interestingness. For example, if there is one region of interestingness that includes records of individuals whose ages range from 10 to 20 years old and who suffer from disease A, and there is another region of interestingness that includes records of individuals whose ages range from 25 to 40 years old and who suffer from disease B, then the existence of a few records of individuals whose ages range from 22-24 years old and who suffer from disease C might be of importance (e.g., disease C may be closely related to diseases A and B). Such candidate records may be recommended based on their proximity to one or more regions of interestingness, which can be computed as the required change in granularity that would need to occur in the dimensions of such records in order to fall within a region of interestingness.

Recommendation module 175 may recommend candidate records by inspecting general-purpose records that fall outside of a region of interestingness and are isolated from other records (e.g., records that are outliers). By using records that are isolated from others, additional research findings may be supported since some patterns may be underrepresented (or not represented at all) in the specific-purpose dataset. Recommendation module 175 may recommend an isolated record based on the degree to which the record is considered an outlier in respect to the rest of the dataset.

Recommendation module 175 may also recommend candidate records by searching for general-purpose records that fall outside of a region of interestingness and are clustered together with other records, as a cluster of records outside of any region of interestingness could indicate a new region of interestingness. In some embodiments, recommendation module 175 calculates the medoid of the cluster of records to be used as a candidate record. A medoid is a point where the average dissimilarity to all other records in the cluster is minimized; thus, a medoid is similar to the geometric concept of a centroid. The medoid may be used as a record that is representative of the cluster of records, and the medoid's granularity may vary depending on the size of the cluster. Some points along the border of the cluster may also be maintained in order to provide information regarding the extent and shape of the cluster.

Consent from the entities associated with the recommended records is requested at operation 280. Researchers may contact the entities corresponding to the recommended records requesting permission to use their personal information at a particular level of granularity. The records may be elevated to the particular level of granularity before requesting authorization so that the entities will know the extent to which their information may be used. In order to increase the likelihood that entities will consent to the use of their data, incentives may be offered. For example, entities from whom consent is sought may be offered monetary incentives like gift cards, or other incentives like prizes, etc. When authorization is received at the level of granularity requested, a recommended record may be included in the research study. In some embodiments, records in the specific-purpose dataset and/or general-purpose dataset may indicate contact information for the corresponding entities. Recommendation module 175 may automatically generate and send a request e-mail using provided contact information in order to obtain permission from the identified entities.

An augmented dataset is generated by combining the specific-purpose dataset with the de-identified general-purpose data and the recommended records for whom consent was obtained at operation 290. The augmented dataset may support the same purpose as the specific-purpose dataset, but since the augmented dataset is larger, it may provide greater utility to researchers. The augmented dataset may be produced by server 140 performing a union operation on the specific-purpose dataset, the de-identified general-purpose data, and the recommended records from consenting entities. The augmented dataset may be output to database 150. In some embodiments, the augmented dataset is stored in database 130 of data mart 120. Researchers may access data mart 120 in order to conduct research for the particular purpose that is supported by the augmented dataset.

Figure 3A:
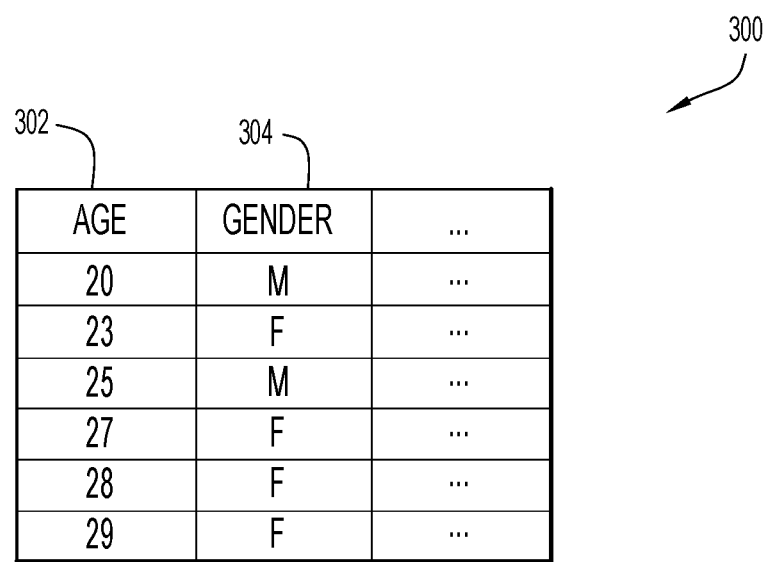
FIGS. 3A-3D illustrate examples of dataset generation using a multidimensional model in accordance with an embodiment of the present invention.
Figure 3B:
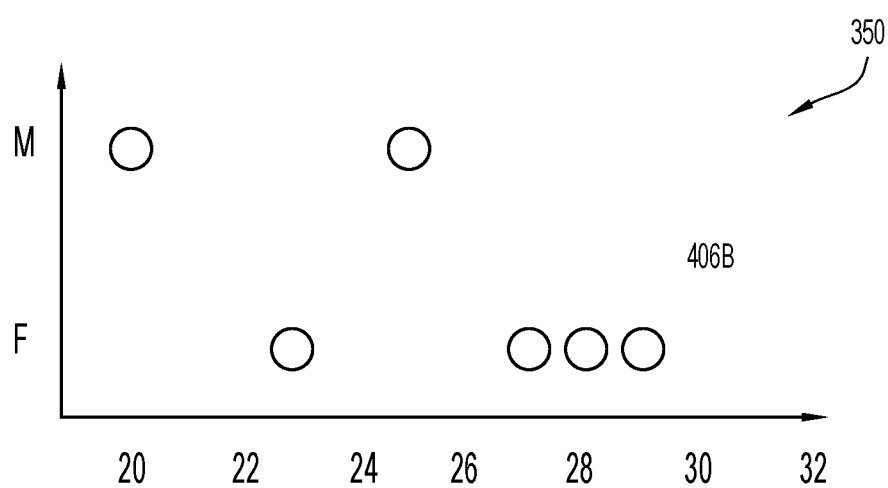
Figure 3C:
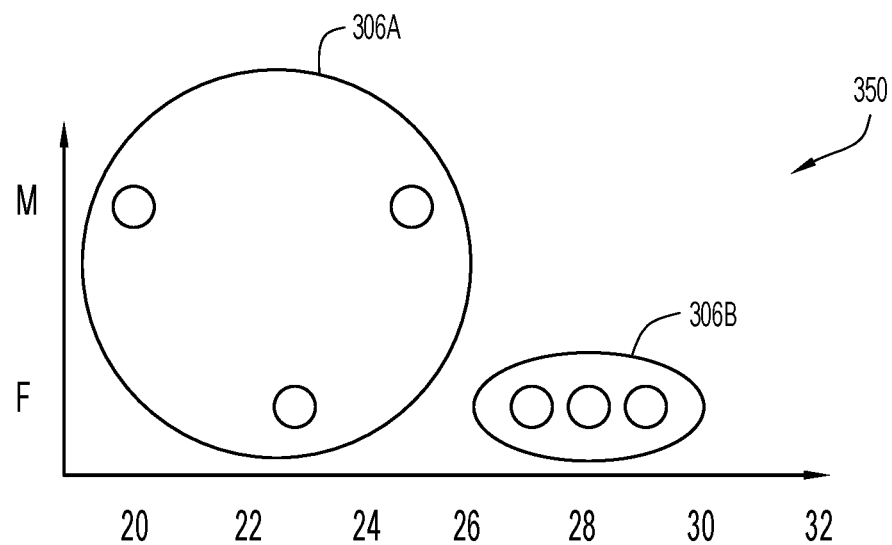
Figure 3D:
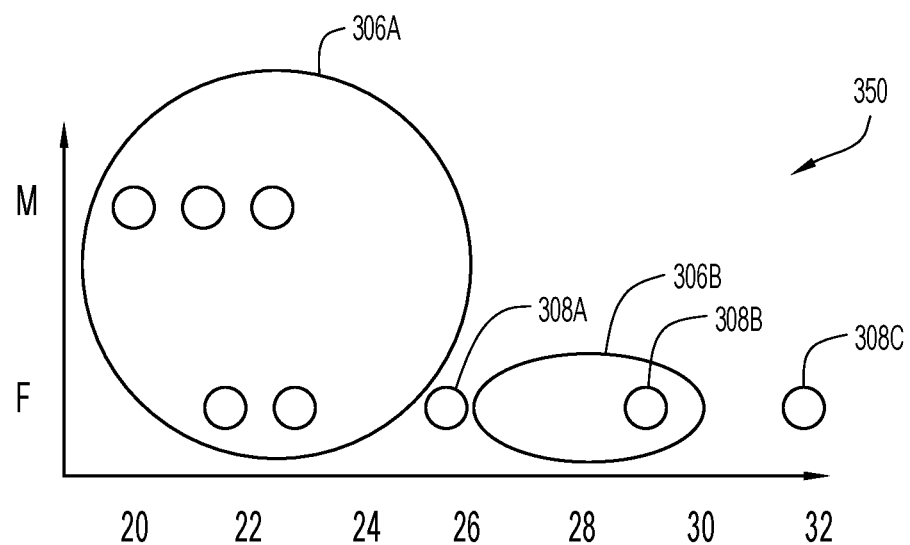

FIGS. 3A-3D illustrate examples of dataset generation using a multidimensional model in accordance with an embodiment of the present invention. FIG. 3A depicts an example of a specific-purpose dataset 300, and FIGS. 3B-3D depict examples of a multidimensional model 350. As depicted, specific-purpose dataset 300 includes six data records with an age field 302 and a gender field 304. Specific-purpose dataset 300 may be populated by records that are provided by individuals who consented to the use of their personal data for one or more specific purposes.

FIG. 3B depicts multidimensional model 350 including records migrated from specific-purpose dataset 300. A multidimensional model may use any quasi-identifiers as dimensions in order to arrange records; as depicted, multidimensional model 350 is a two-dimensional model with the quasi-identifiers of "age" and "gender" selected for its dimensions. The six records from specific-purpose dataset 300 have been represented in multidimensional model 350 as the six points.

FIG. 3C depicts multidimensional model 350 with partitions made to separate a dataset into regions of interestingness, such as regions of interestingness 306A and 306B. In some embodiments, ROI module 160 partitions the dataset into the regions of interestingness according to the clustering of records. For example, the dataset is partitioned such that region of interestingness 306A has contains six records and region of interestingness 306B contains three records.

FIG. 3D depicts data records from the general-purpose dataset fitted into the multidimensional model 350 with the regions of interestingness from the specific-purpose dataset overlayed. A subset of data records from the general-purpose data are selected because they fall into a region of interestingness. For example, the five records that fall into region of interestingness 306A may, after de-identification, be included in the resulting augmented dataset. Some records may be initially removed even though they fit within a region of interestingness. For example, record 308B may be initially removed because a single record cannot be de-identified. Some records, such as 308A and 308C, may be initially removed because they do not fall within any region of interestingness. The remaining records from the general-purpose dataset are then de-identified inside of each partition. For example, instead of de-identifying all of the records, the records within region of interestingness 306A will be de-identified together.

Although records 308A, 308B, and 308C may be initially discarded, these records may be included in the final augmented data set upon elevating the records to an appropriate level of granularity and receiving authorization from the entity corresponding to each record. For example, record 308A may be a candidate record because it is located between two regions of interestingness. Record 308B may be a candidate record because it falls within a region of interestingness but cannot be de-identified; if authorization is granted by the entity corresponding to record 308B, then record 308B can be included in the resulting augmented dataset. Record 308C may represent an outlier and may thus be a candidate for inclusion in the augmented dataset, since outliers may support additional research findings.

Figure 4:
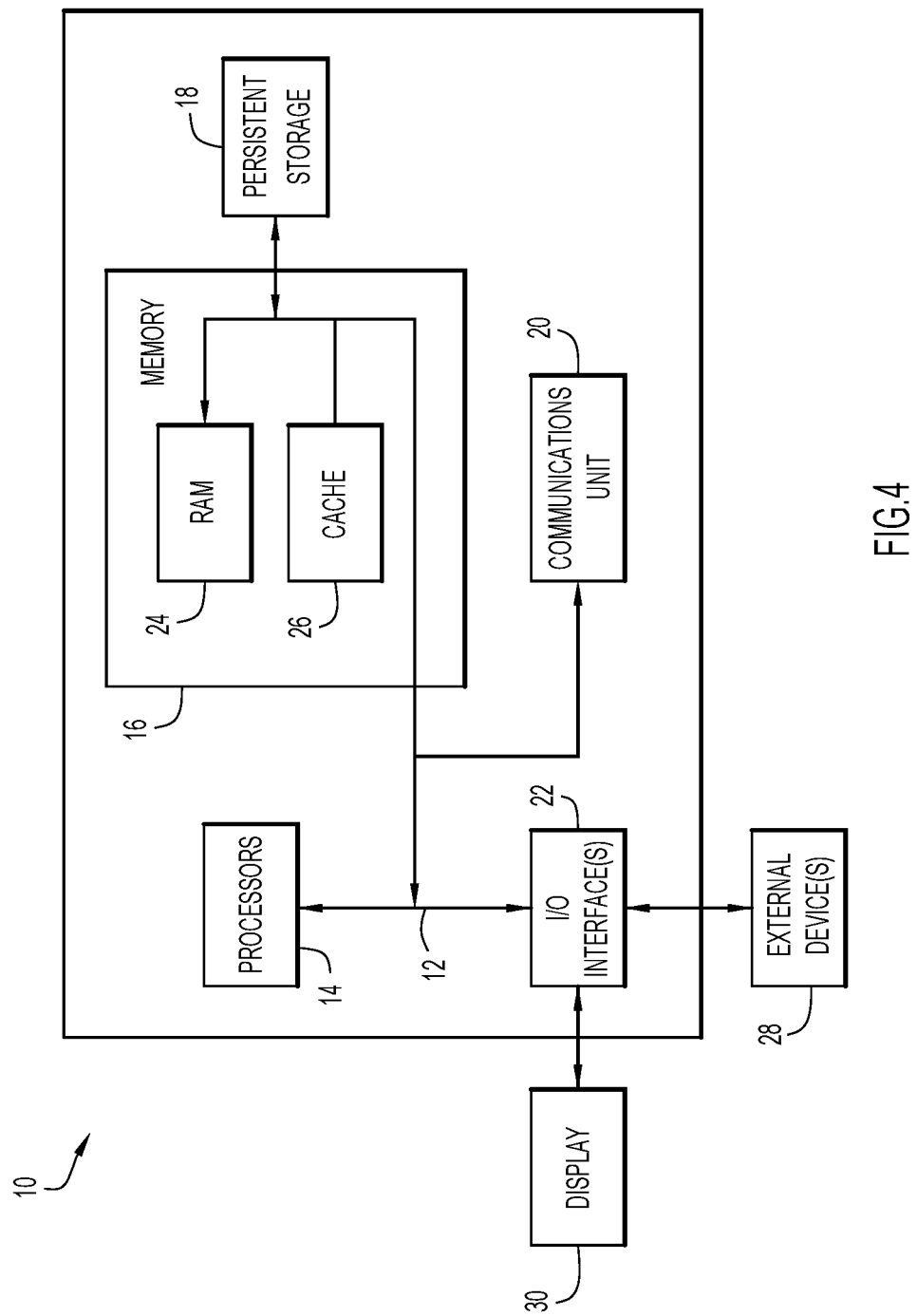
FIG. 4 is a block diagram depicting a computing device in accordance with an embodiment of the present invention.

FIG. 4 is a block diagram depicting components of a computer 10 suitable for executing the methods disclosed herein. Computer 10 may enable server 140 to perform dataset augmentation in accordance with embodiments of the present invention. It should be appreciated that FIG. 4 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data in any dataset and a common data model, whether de-identified not, may be stored within any conventional or other data structures (e.g., files, arrays, lists, stacks, queues, records, etc.) and may be stored in any desired storage unit (e.g., database, data or other repositories, queue, etc.) The data transmitted between user device 110, database 120, and de-identification server 140 may include any desired format and arrangement, and may include any quantity of any types of fields of any size to store the data. The definition and data model for any datasets and common data models may indicate the overall structure in any desired fashion (e.g., computer-related languages, graphical representation, listing, etc.).

Data in a dataset, such as a general-purpose dataset, specific-purpose dataset, or augmented dataset, may include any information provided to data lake 105, data mart 120, and/or server 140. Data in a dataset or common data model may include any desired format and arrangement, and may include any quantity of any types of fields of any size to store any desired data. The fields may indicate the presence, absence, actual values, or any other desired characteristics of the data of interest (e.g., quantity, value ranges, etc.). Data in a dataset or common data model may include all or any desired portion (e.g., any quantity of specific fields) of personal information (PI) or other data of interest within a given implementation or system. Data in a dataset or common data model may indicate the overall structure in any desired fashion (e.g., computer-related languages, graphical representation, listing, etc.). The fields for the dataset or fields and tables in a common data model may be selected automatically (e.g., based on metadata, common or pre-defined models or structures, etc.) or manually (e.g., pre-defined, supplied by a data owner, etc.) in any desired fashion for a particular implementation or system. Metadata (e.g., for field selection, common model, etc.) may include any suitable information providing a description of fields or information (e.g., description of content, data type, etc.).

The data in a dataset may include any data collected about entities by any collection method, any combination of collected information, any information derived from analyzing collected information, and any combination data before or after de-identification.

The present invention embodiments may employ any number of any type of user interface (e.g., Graphical User Interface (GUI), command-line, prompt, etc.) for obtaining or providing information (e.g., data in a dataset or common data model), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for generation and analysis of various types of data, even in the absence of that data. For example, present invention embodiments may be utilized for any types of data interest (e.g, sensitive data (personal information (PI) including information pertaining to patients, customers, suppliers, citizens, and/or employees, etc.) non-sensitive data, data that may become unavailable (e.g., data that is subject to deletion after retention for a minimum time interval (e.g., information subject to various regulations, etc.), information that becomes unavailable due to system outage, power failure, or other data loss, etc.), etc.). Further, present invention embodiments may generate and utilize any quantity of data regarding entities of interest.

It will be appreciated that the embodiments described above and illustrated in the drawings represent only a few of the many ways of augmenting a dataset using de-identified data and selected authorized records.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, region of interestingness module 160, data relevancy module 165, de-identification module 170, recommendation module 175, etc.). These systems may include any types of monitors and input devices (e.g., keyboard, mouse, voice recognition, etc.) to enter and/or view information.

It is to be understood that the software (e.g., server software, communication software, database software, ROI module 160, data relevancy module 165, de-identification module 170, recommendation module 175) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., server software, communication software, database software, ROI module 160, data relevancy module 165, de-identification module 170, recommendation module 175) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data in a dataset). The database system may be implemented by any number of any conventional or other databases, data stores or storage structures (e.g., files, databases, data structures, data or other repositories, etc.) to store information (e.g., data in a dataset). The database system may be included within or coupled to the server and/or client systems. The database systems and/or storage structures may be remote from or local to the computer or other processing systems, and may store any desired data (e.g., data in a dataset).

The present invention embodiments may employ any number of any type of user interface (e.g., Graphical User Interface (GUI), command-line, prompt, etc.) for obtaining or providing information (e.g., data in a dataset), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer system for migrating and de-identifying data, the computer system comprising:
one or more computer processors;
one or more computer readable storage media;
program instructions stored on the one or more computer readable storage media for execution by at least one of the one or more computer processors, the program instructions comprising instructions to:

determine one or more regions of interestingness within a model of a first set of data records, wherein the first set of data records are authorized for a research study by associated entities and contain a plurality of direct identifiers and quasi-identifiers of the associated entities, wherein the one or more regions of interestingness are determined based on the values of the plurality of direct identifiers and quasi-identifiers;

represent within the model a second set of data records, wherein the second set of data records are relevant for supporting objectives of the research study, correspond to entities other than those associated with the first set of data records, and are used after de-identification according to de-identification requirements or authorization by corresponding entities;

identify data records from the second set of data records that are particularly useful and have greater relevance for supporting the objectives of the research study based on the model;

request authorization from the corresponding entities of the identified data records from the second set of data records, wherein requests for authorization are automatically generated and sent to the corresponding entities via a network; and generate a resulting dataset for the research study by including the data records of the first set of data records within selected regions of interestingness and the identified data records of the second set of data records after receiving the requested authorization via the network.

2. The computer system of claim 1, wherein identifying data records from the second set of data records further comprises:
identifying data records of the second set of data records that are within the one or more regions of interestingness and their de-identification, according to the de-identification requirements, provides significant utility loss for the research study.

3. The computer system of claim 1, wherein identifying data records from the second set of data records further comprises:
identifying data records of the second set of data records that are outside the one or more regions of interestingness.

4. The computer system of claim 1, wherein requesting authorization further comprises:
offering an incentive to the corresponding entities of the identified data records from the second set of data records for providing consent for the use of the identified data records of the corresponding entities to support the research study.

5. The computer system of claim 1, wherein requesting authorization further comprises:
requesting consent from the corresponding entities of the identified data records from the second set of data records for using their data, after they have been elevated to a corresponding level of a determined granularity.

6. The computer system of claim 5, wherein the resulting dataset includes the identified data records of the second set of data records after receiving the requested consent from the corresponding entities and elevating those data records to the level of determined granularity.

7. The computer system of claim 6, wherein the resulting dataset further includes a number of other data records of the second set of data records after being de-identified based on the de-identification requirements.

8. A computer program product for migrating and de-identifying data, the computer program product comprising one or more computer readable storage media collectively having program instructions embodied therewith, the program instructions executable by a computer to cause the computer to:
determine one or more regions of interestingness within a model of a first set of data records, wherein the first set of data records are authorized for a research study by associated entities and contain a plurality of direct identifiers and quasi-identifiers of the associated entities, wherein the one or more regions of interestingness are determined based on the values of the plurality of direct identifiers and quasi-identifiers;

represent within the model a second set of data records, wherein the second set of data records are relevant for supporting objectives of the research study, correspond to entities other than those associated with the first set of data records, and used after de-identification according to de-identification requirements or authorization by corresponding entities;

identify data records from the second set of data records that are particularly useful and have greater relevance for supporting the objectives of the research study based on the model;

request authorization from the corresponding entities of the identified data records from the second set of data records, wherein requests for authorization are automatically generated and sent to the corresponding entities via a network; and generate a resulting dataset for the research study by including the data records of the first set of data records within selected regions of interestingness and the identified data records of the second set of data records after receiving the requested authorization via the network.

9. The computer program product of claim 8, wherein identifying data records from the second set of data records further comprises:
identifying data records of the second set of data records that are within the one or more regions of interestingness and their de-identification, according to the de-identification requirements, provides significant utility loss for the research study.

10. The computer program product of claim 8, wherein identifying data records from the second set of data records further comprises:
identifying data records of the second set of data records that are outside the one or more regions of interestingness.

11. The computer program product of claim 8, wherein requesting authorization further comprises:
requesting consent from the corresponding entities of the identified data records from the second set of data records for using their data, after they have been elevated to a corresponding level of a determined granularity.

12. The computer program product of claim 11, wherein the resulting dataset includes the identified data records of the second set of data records after receiving the requested consent from the corresponding entities and elevating those data records to the level of determined granularity.

13. The computer program product of claim 12, wherein the resulting dataset further includes a number of other data records of the second set of data records after being de-identified based on the de-identification requirements.

14. The computer program product of claim 8, wherein requesting authorization further comprises:

offering an incentive to the corresponding entities of the identified data records from the second set of data records for providing consent for the use of the identified data records of the corresponding entities to support the research study.

* * * * *